(12) United States Patent  (10) Patent No.: US 6,709,149 B1
Tepic  (45) Date of Patent: Mar. 23, 2004

(54) METHOD OF BONE CEMENT PREPARATION

(75) Inventor: Slobodan Tepic, Zurich (CH)

(73) Assignee: AO Research Institute Davos, Davos (CH)

( * ) Notice: Subject to any disclaimer, the term of this patent is extended or adjusted under 35 U.S.C. 154(b) by 0 days.

(21) Appl. No.: 09/868,116
(22) PCT Filed: Dec. 14, 1998
(86) PCT No.: PCT/EP98/08199
 § 371 (c)(1),
 (2), (4) Date: Jun. 14, 2001
(87) PCT Pub. No.: WO00/35506
 PCT Pub. Date: Jun. 22, 2000
(51) Int. Cl.[7] ................................................. A61L 24/06
(52) U.S. Cl. ..................................... 366/139; 366/163.1
(58) Field of Search ............................. 366/139, 163.1, 366/348; 523/116; 606/92–94

(56) References Cited

U.S. PATENT DOCUMENTS

| | | | |
|---|---|---|---|
| 4,239,113 A | | 12/1980 | Gross et al. |
| 4,463,875 A | * | 8/1984 | Tepic |
| 4,808,184 A | | 2/1989 | Tepic |
| 4,973,168 A | * | 11/1990 | Chan |
| 5,051,482 A | * | 9/1991 | Tepic |
| 5,328,262 A | * | 7/1994 | Lidgren et al. |
| 5,588,745 A | | 12/1996 | Tanaka et al. |
| 6,024,480 A | * | 2/2000 | Seaton et al. |

FOREIGN PATENT DOCUMENTS

| DE | 196 41 775 A1 | 2/1998 |
|---|---|---|
| GB | 1 583 937 A | 2/1981 |

OTHER PUBLICATIONS

WO 97/18031, Publication Date: May 22, 1997, Method and Device for Feeding Components for Bone Cement into a Mixing Vessel for these.

WO/88/03811, Publication Date: Jun. 2, 1988, Method and Apparatus for Preparing a Self–Curing Two–Component Powder Liquid Bone Cement.

* cited by examiner

Primary Examiner—Charles E. Cooley
Assistant Examiner—David Sorkin
(74) Attorney, Agent, or Firm—Rankin, Hill, Porter & Clark LLP

(57) ABSTRACT

A method of bone cement preparation from a polymeric powder and a liquid component including a polymerisable monomer or comonomer by the action of a catalytic system. Particles of the powder are packed in a powder container having an inlet and an outlet port, while the liquid component is held in a liquid container. The liquid container is connected to te inlet port and a vacuum source is connected to the outlet port. A voided space between the powder particles is flooded by the liquid component that flows form the inlet port toward the outlet port under the influence of the vacuum source.

19 Claims, 11 Drawing Sheets

METHOD OF BONE CEMENT PREPARATION

This invention relates to a method of bone cement preparation. It further relates to a bone cement mixture obtained by said method and an apparatus for performing said method.

The invention allows for preparation of a pore-free, mechanically superior bone cement, in a closed system that requires minimal human intervention, and delivers a consistent, operator-independent performance.

Surgical bone cement is commonly used for fixation of joint prosthesis, most frequently in total hip and total knee replacement. It is prepared by mixing a powder component, comprising emulsion polymerized polymethylmethacrylate (PMMA), with a methyl-methacrylate (MMA)-based liquid. The conventional catalytic system for the room temperature curing resins is based on the chemical decomposition of benzoyl peroxide by an accelerator, N,N-dimethyl-p-toluidine. Decomposition of benzoyl peroxide releases free (phenyl) radicals and initiates polymerization of MMA. Benzoyl peroxide is either residual, i.e. left over from the polymerization of the PMMA powder, or is added in powder form to PMMA. The accelerator is added to MMA liquid, which, at the least, also contains radical scavenger hydroquinone to prevent accidental polymerization.

In conventional bone cements, introduced to total hip replacement (THR) surgery by Dr. John Charnley in the early sixties, the powder and the liquid components are mixed together, either by a spatula in a simple bowl, or in dedicated mixing/delivery devices. Increase in the clinical use of dedicated mixing devices has been driven by mostly two factors: (i) hand mixing in open air leads to air bubble inclusions which significantly reduce the strength of bone cement; (ii) undesirable exposure of the operating room personnel to monomer vapours. Pores within the bone cement mantle, caused mostly by inclusion of air bubbles during mixing, reduce its fatigue strength, which is now generally accepted to be a major risk factor in aseptic loosening of cemented prosthetic components.

Mixing of the powder and the liquid aims at full wetting of the powder, i.e. all beads should be surrounded by the liquid. Upon decomposition of benzoyl peroxide and release of free radicals, monomer polymerizes with nucleation on the partially dissolved surface of the beads. The amount of monomer relative to powder is thus determined by predominantly physical, rather than chemical considerations. Three characteristics of polymerization effect the outcome and set the limitations on the possible improvements. Polymerization is:

(i) exothermic:
  polymerization of MMA into PMMA releases a fixed amount of heat per mole (55,6 kJ/mol). Release of polymerization heat could increase the temperature of the bone cement mixture by more than 100 deg C, but due to heat transfer into surrounding tissues and the prosthesis, temperatures at the interface to bone rarely exceed 60 deg C. The ratio of monomer to polymer is an important factor influencing final temperature increase. Less monomer to polymerize means less heat released, and the more polymer there is to warm up, the lower the temperature. Bone cement according to this invention uses about 20% less monomer than conventional hand mixing formulations, which results in reduced peak temperatures (by about 8 degrees C).

(ii) density increasing:
  density of MMA monomer is 943 kg/m$^3$, density of the polymer is 1180 kg/m$^3$, i.e. polymerization is associated with volumetric shrinkage of about 20%. With a typical ratio of polymer to monomer of 2,1:1, this leads to an expected cured cement shrinkage of about 6,5%. However, the ultimate, experimentally measurable, volumetric shrinkage depends on other factors, most importantly on the amount of pores within the cement. Presence of pores allows for shrinkage to be compensated from within, i.e. the pores get larger and the volume change measured from outside is less than if the cement were pore-free. In general, all methods deployed to reduce cement porosity lead to an increase in shrinkage. Reduced use of monomer in the cement of this invention is of an advantage here as well; about 1% less shrinkage is expected, other factors (i.e. cement and sample preparation technique) being the same.

(iii) incomplete:
  polymerization process depends on formation of free radicals to initiate it, nucleation on the extant polymer surfaces and availability of monomer molecules to extend the growing chains. In all cases, a number of monomer molecules will not find their way into polymer chains and will thus remain as residual monomer within the polymerized matrix. Polymerization process will continue at a very limited rate even after most of the polymer matrix is formed due to mobility of monomer molecules through the polymerized matrix. That same mobility allows monomer to leach out of the cured cement. This is deemed undesirable in view of tissue compatibility. The range of residual monomer found in commercial cements right after preparation is about 2 to 6% (monomer weight per total weight). In time (with quasiequilibrium reached in 2 to 4 weeks) this is reduced to less than 0,5% due to combined effects of continuing polymerization, migration and release of free monomer. Again, reduced use of monomer in the cement of this invention is of an advantage here as well; less monomer to start with leads to a lower residue (about 20% compared to the best selling regular viscosity cement).

In the early eighties the shortcomings of hand mixing and delivery of bone cement became widely acknowledged. With the first long term studies of improved cementing techniques becoming available, showing better clinical results than traditional hand mixing/hand application, the interest for, and clinical use of various systems for bone cement preparation has been steadily increasing. Disappointments with the clinical outcomes of cementless prosthesis have also contributed to re-establishment of cemented total joint replacement as a standard procedure, especially for the femoral component of the total hip replacement and for total knee prosthesis.

All known, commercially available and clinically used mixing systems are designed to remove air inclusions which are invariably introduced at the time when the liquid and powdered components are brought into contact. This task can only be partially accomplished due to mostly time limitations imposed by dissolution of PMMA in MMA and kinetics of polymerization.

Centrifuging:
  Championed by Dr. William Harris, Boston, centrifuging was found to be partially effective in reducing the porosity of certain commercial brands of bone cement. While centrifuging could be used with some of the existing cements, it required cumbersome equipment, chilling of cement (to reduce viscosity and prolong setting time) and tight coordination of operating room personnel. It has found rather limited clinical acceptance in the U.S. and even less in Europe. The use of the bottom-up filling technique for the femur by means of a caulking gun, syringe and a long nozzle, as well as pre-plugging of the femoral canal to allow for cement pressurizing have also been introduced by Dr. Harris. Currently, both, the older top-down and the bottom-up filling technique are used in Europe; in the U.S. the latter is dominant.

Partial Vacuum Mixing:

Developed and brought into clinical use by Dr. Lars Lidgren, Lund, this technique was adopted from the dental field where the same materials have been used for decades before introduction into orthopaedics. In molding of dentures from MMA/PMMA resins, air entrapment has also been recognized as undesirable; here less for reduction of strength than for difficulties of hygiene maintenance in dentures with pores which may be open to the surface. Mixing the cement in a bowl under partial vacuum (of some 100 mbar) reduces the porosity of the material cured at atmospheric, or elevated pressure. Partial vacuum mixing systems have found the widest clinical acceptance. Regular viscosity cements, such as Palacos R, are usually chilled (to reduce viscosity and prolong the setting time) for preparation in these systems and for extrusion through the nozzle in bottom-up delivery.

Laboratory tests show improved fatigue properties of partial vacuum mixed cements, but clinical long term studies do not support expectations. The reasons for this are obscure at the moment, but there are indications that the learning curve in the widespread use of partial vacuum mixing systems may explain this discrepancy; surgery departments that have used such systems for longer times show better outcomes than the newcomers.

Pre-pressurizing:

Developed by Dr. K. Draenert, Munich, pre-pressurizing of the bone cement aims at reducing porosity by prolonged application of pressure onto the mixed cement. While the pores are reduced during the application of pressure within the syringe, most of the effect is lost upon extrusion of the cement into the bone, where it cannot be substantially pressurized. Some benefit could be expected due to expansion of pressurized air within the pores in terms of compensating for the polymerization shrinkage, but this is very much subject to timing and viscosity of the cement. Overall, pre-pressurizing is probably the least effective measure for porosity reduction (even in laboratory tests done under optimal conditions). Dr. Draenart has subsequently expanded his original system to incorporate partial vacuum mixing, as well as pre-pressurizing.

Clinical practice, is dominated by various systems for partial vacuum mixing. The basic limitation is imposed by the level of vacuum under which mixing can be carried out. At room temperature, MMA monomer will boil at 38 mbar. Most systems are designed to operate at about 100 mbar. This leaves a significant amount of residual air entrapped in the mixed cement; once the mixture is brought back to atmospheric pressure, air inclusions shrink, say by factor 10 to 20, but pores in fact do persist—they are only reduced in size. This improves mechanical properties, including fatigue strength, but mostly by the increase in the effective cross section and less by reduction in stress concentration which is not so much influenced by the size of pores.

From WO88/03811 TEPIC a vacuum flooding system is known which is essentially free of air inclusions, but the requirement for high vacuum in that system is technically difficult to achieve.

Following the basic principles of the method according to the present invention—vacuum-induced flooding of the powder and draining of excess liquid—are described in detail. In contrast to other known bone cement preparation systems, the present invention aims at avoiding inclusion of air, rather than allowing for it, and then reducing it. This is accomplished by pre-packing the powder into a syringe, and then drawing the liquid through the powder column by vacuum. As the fluid moves into the powder column residual air in front of the flooding front is pulled away by the vacuum. The end result is that the residual air between the particles of powder is replaced by the cement liquid. The process leads to full wetting contact between the beads and the liquid, rendering any mechanical mixing superfluous.

Because of high solubility of benzoyl peroxide in MMA, benzoyl peroxide should preferably not be added in powdered form. Flooding of powder would result in a gradient of catalyst and lead to uneven polymerization. However, emulsion polymerized PMMA powders can be produced with residue of benzoyl peroxide which upon dissolution of the surface layer of the beads becomes available for the reaction with toluidine. Use of such powders with sufficient residue of benzoyl peroxide (with an average value in the range of 1,0% to 2,5%) allows for flooding of a packed powder column with only a slight gradient in concentrations of the catalytic system components.

Deployment of vacuum-induced, controlled flooding eliminates the need for mixing, and removes a major source of variability in cement preparation. Solubility of the PMMA powder leads to additional packing (consolidation) of the column after flooding, which creates a small excess of monomer at the inlet side of the syringe. This excess is expelled (back into the ampoule) by the action of a pneumatically driven piston before the cement syringe is removed from the vacuum pump and placed on the caulking gun for extrusion. Since the syringe ports for vacuum and liquid are provided with screens which do not allow any loss of powder, the action of the pneumatic piston leads to draining of the cement mixture (from any excess monomer). This also provides for the reduced ultimate content of monomer (by about 20%), which in other mixed cements must be present in excess in order to allow for better wetting.

Besides methylmethacrylate other suitable polymerisable monomers or comonomers may be used as e.g. ethyl-methacrylate or butyl-methacrylate or mixtures of such methacrylates.

The vacuum source should be able to generate a vacuum in the range of 10 to 200 mbar, preferably in the range of 50 to 100 mbar.

Figure 1:
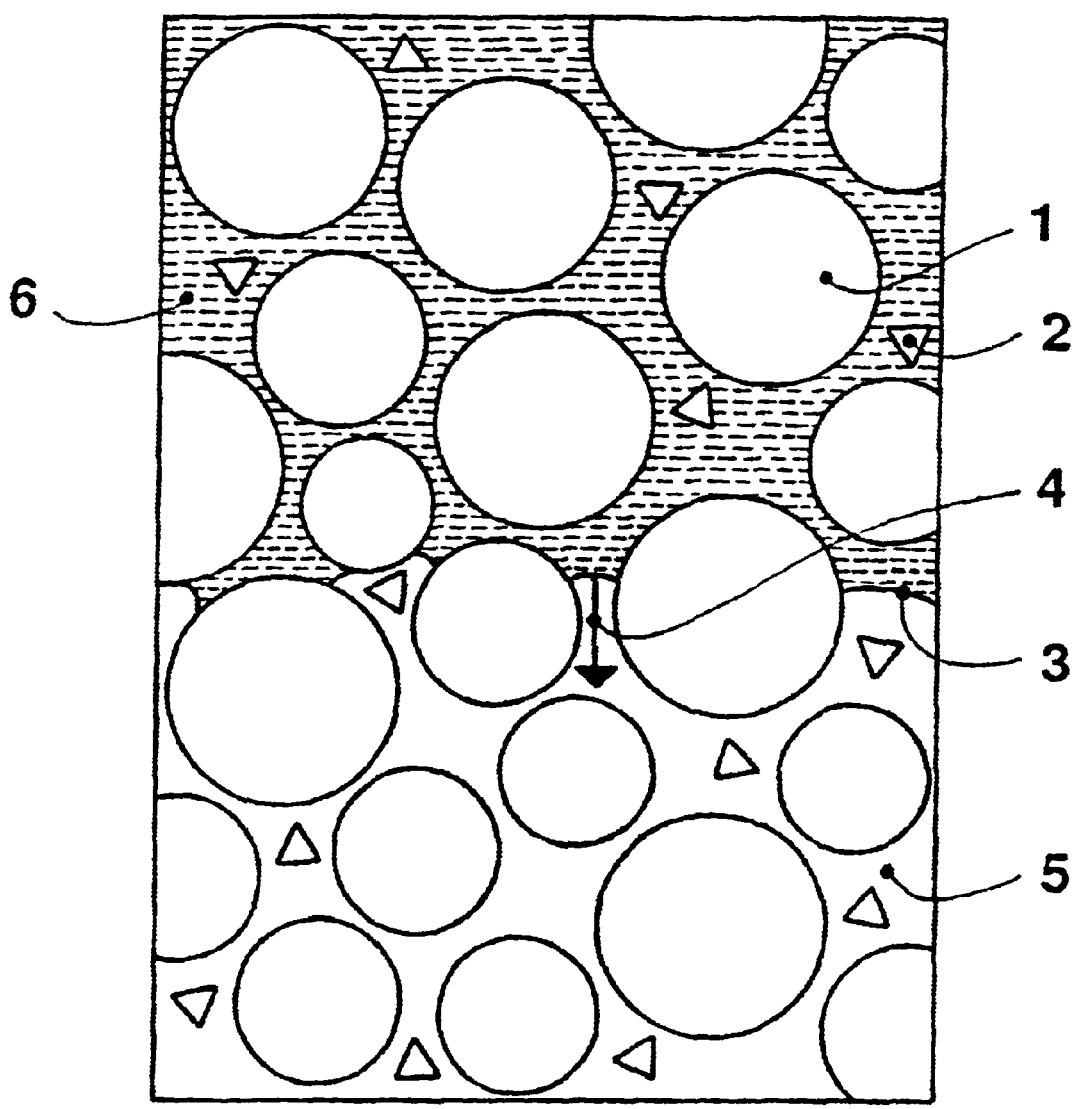
FIG. 1 is a schematic representation of the movement of the monomer flooding front through the powder column under influence of vacuum for the method according to the invention.

The principal process of bone cement preparation according to the present invention is orderly replacement of the residual air in the interspaces of the powder component by the liquid component. During this so-called flooding phase, FIG. 1, the powder column with PMMA beads 1 and additives 2 (such as zirconium dioxide and antibiotic) is divided in two sections separated by the flooding front 3. Flooding front 3 sweeps the volume of the powder in the direction 4 driven by a pressure gradient created by reduced pressure (vacuum) in the unflooded interspaces 5 as compared to flooded interspaces 6. Experimental work has shown that creating the flooding pressure gradient by increasing the pressure of the liquid instead of reducing the pressure of the air leads to disorderly flooding, whereby the flooding front will advance unevenly and lead to entrapment of air.

Figure 2:
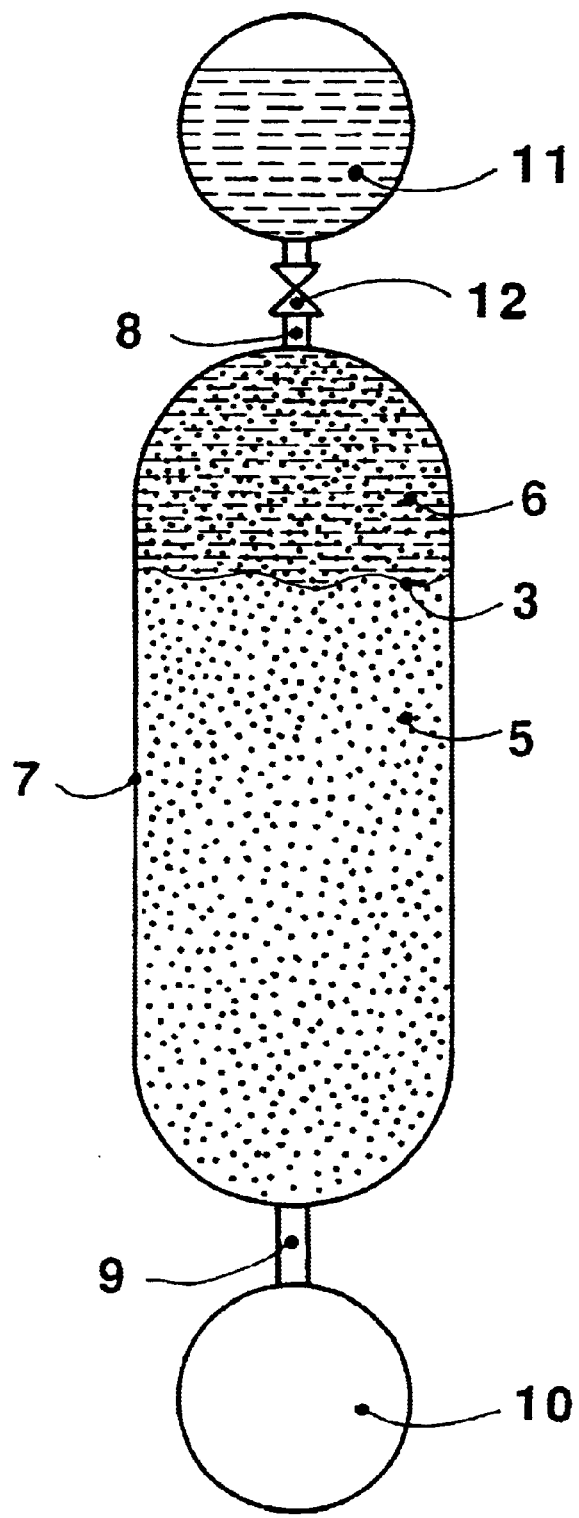
FIG. 2 is a schematic representation of the principal features of the powder container of the apparatus according to the invention.

In order for the flooding front 3 to completely sweep the volume of the powder container 7, FIG. 2, it is necessary to maintain evacuation of the unflooded interspaces 5 throughout the flooding phase. Hence the container 7 is provided with two ports: an inlet or upstream port 8 and an outlet or downstream port 9. Both ports must be designed so as to effectively confine the powder to the container 7 prior to and during cement preparation. Additionally, the inlet port 8 must allow for relatively easy flow of monomer, and the outlet port 9 for easy flow of air.

Flooding is effected by connecting the outlet port 9 to a vacuum source 10 and the inlet port 8 to a monomer container 11. Since no mixing is needed for a PMMA based bone cement prepared according to this invention, container 7 is preferably inflexible and completely filled with powder. Inlet port 8 may optionally be supplied by a valve 12, which is operated either manually or automatically, responding to the pressure difference between the evacuated powder container 7 (at the inlet port 8) and the monomer container 11 (which is essentially at the atmospheric pressure). The valve 12 could be used to prevent the flow of monomer before a certain level of vacuum in the powder is achieved. Experiments have shown that permeability of the powder column to air is sufficient to allow a high capacity vacuum pump to reduce the pressure of the residual air fast enough to attain excellent results even if monomer flow is not held back by means of a valve.

Figure 3:
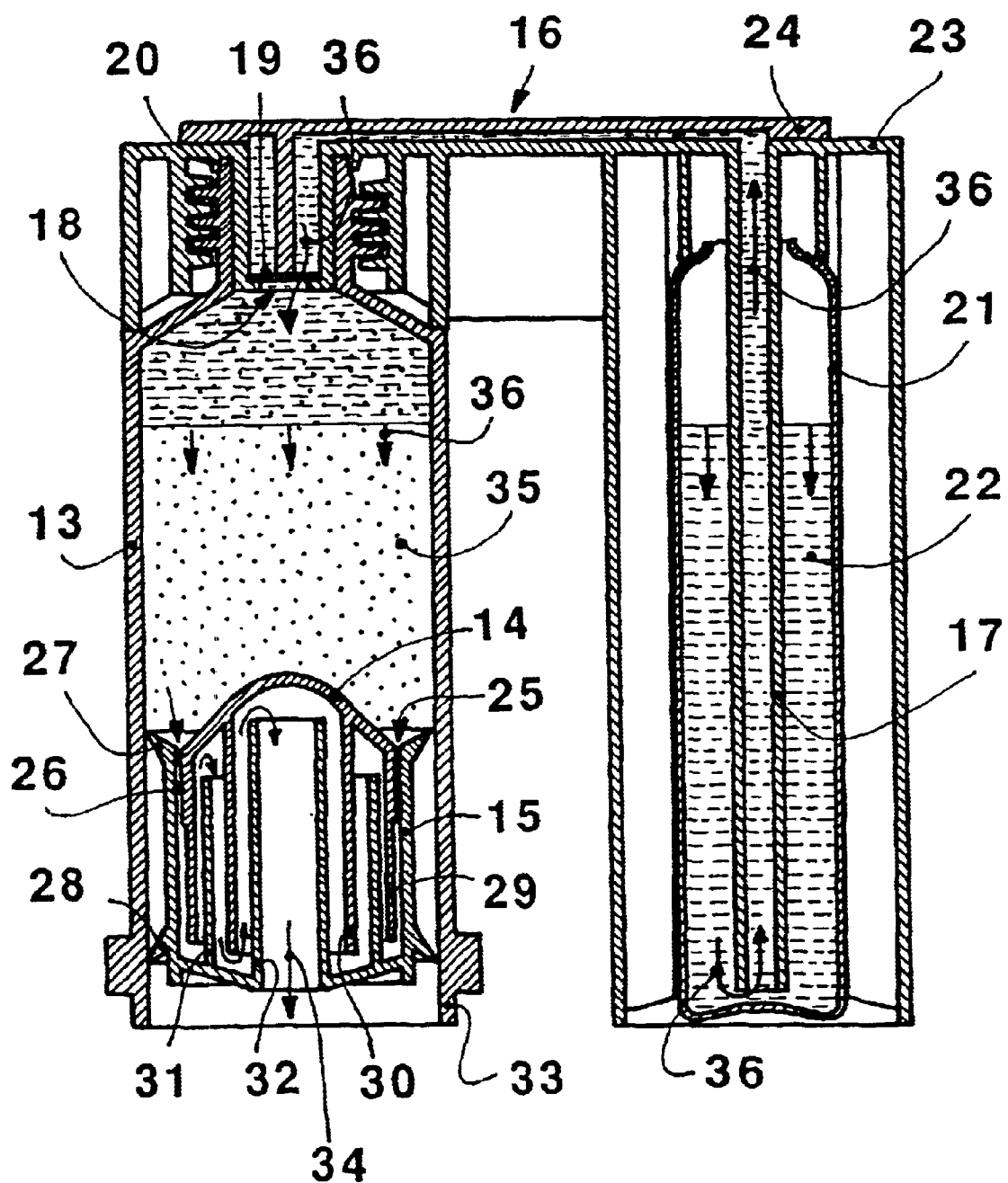
FIG. 3 is a section through a preferred embodiment of the powder container of the apparatus according to the invention.

A preferred embodiment of the powder container is shown in detail in FIG. 3. Powder container consists of a syringe 13, a two part piston 14 and 15, and an ampoule adapter 16. Adapter 16 is screwed onto the syringe 13. Construction of the adapter 16 provides for a connection between the monomer suction tube 17 and the inlet port 18, which is covered by a fine stainless steel mesh 19. When fully screwed-on, adapter 16 is hermetically sealed to the syringe 13 by a seal 20. The ampoule 21 filled with monomer 22 is opened and inserted into adapter 16 so that the suction tube 17 reaches near the bottom of the ampoule. The mesh 19 is tightly woven with sub-micron openings; this prevents even the smallest of powder particles to cross it. However, resistance to monomer flow is very low. Adapter 16 is constructed from three separate plastic components: the suction tube 17, the main body 23 and the cover plate 24, which are ultrasonically welded together with the mesh 19.

The two piston components, the cap 14, and the seals section 15, are pressed together along the perimeter 25. At this aspect the piston cap 14 is provided with micro-ribs 26 about 50 micrometers deep, Detail A. This results in a controlled width gap separating the components 14 and 15. This gap is the downstream, or outlet port 9 from the powder compartment 7 of FIG. 2. The mesh 19 corresponds to the upstream, or the inlet port 8 of FIG. 2.

Piston is sealed inside the syringe 13 by two lips 27 and 28. The cylindrical sections 29 and 30 of the piston cap 14, and 31 and 32 of the seals section 15, form a labyrinth which prevents easy spilling of any monomer which may enter the piston at the end of flooding phase. The bottom section 33 of the syringe 13 is sealed into the vacuum pump which evacuates the powder column in the powder compartment 35 of the syringe 13, as indicated by arrows 34. Monomer flow is indicated by arrows 36.

Powder column in the powder compartment 35 is packed to a pre-determined density. Since permeability of the column depends on the fractional porosity P and on the total surface S of the particles in a unit volume according to Kozeny's equation:

$$k = \frac{1}{5}[p^3/(1-p)^2]/s^2$$

it is important to control the powder packing process. If the powder were loosely packed it could undergo further compaction in transport and handling which would lead to uneven flooding; too tight packing would slow down flooding. Powder bead size distribution must also be precisely controlled; very fine, dust like particles of PMMA are not permitted, less monomer viscosity would increase too quickly and prevent complete flooding.

Bone cement formulation which was selected for the procedure, contains 10% by weight of zirconium dioxide and approximately 2,5% of Gentamycin sulphate. Optimal packing results in a powder column of fractional porosity P=0,36 and leads to about 30 seconds flooding time for 63 grams of powder. Acceptable range for P is 0,34 to 0,38.

A Preferred Method of Preparation of the Bone Cement Comprises a Four Step Procedure:

Step 1: Flooding

Figure 4:
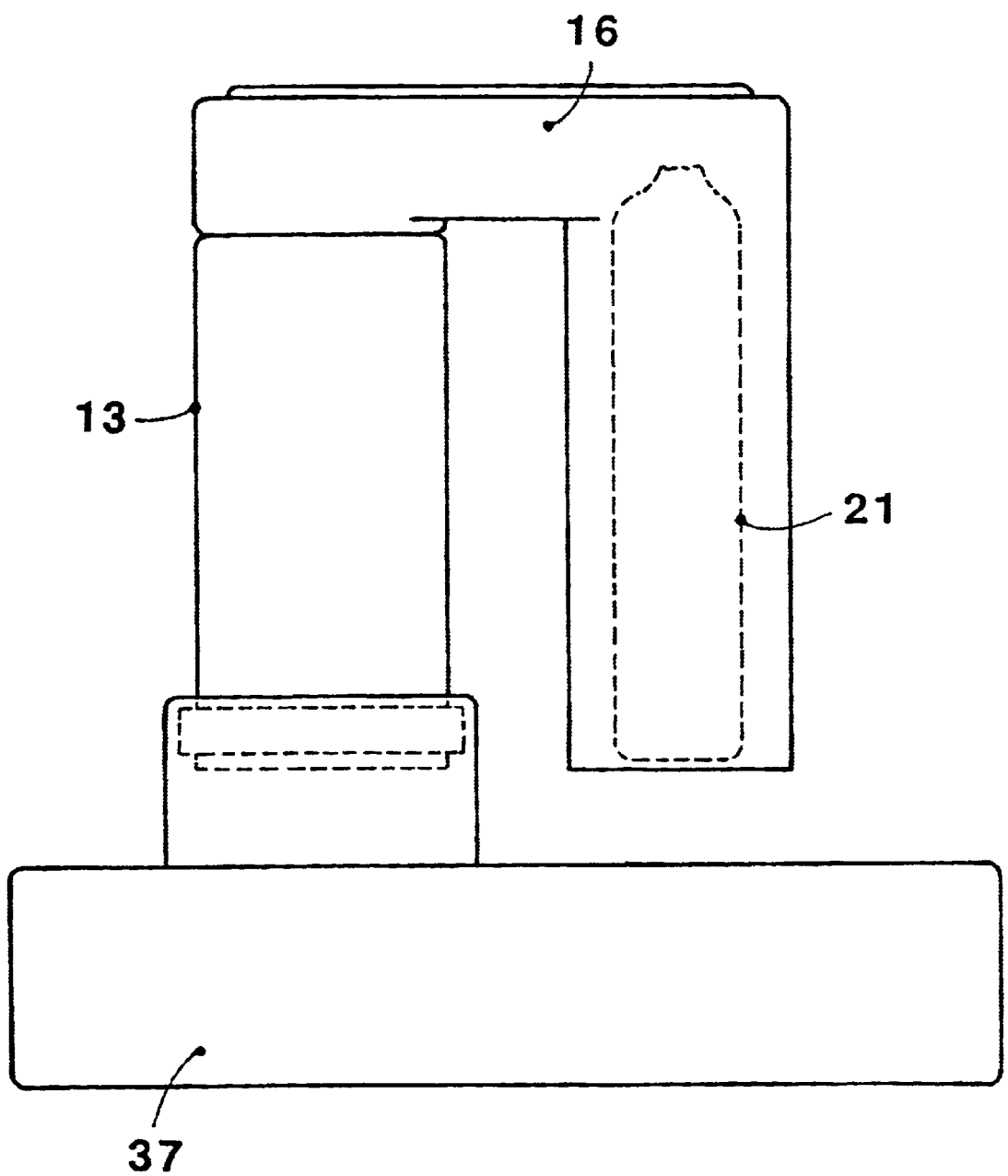
FIG. 4 is a schematic representation of the bone cement flooding on the vacuum pump.

Monomer ampoule 21 is opened, placed within the adapter 16, and the whole assembly is then connected to a vacuum source, e.g. a compressed air-driven (Venturi type) vacuum pump 37, FIG. 4. Vacuum pump 37 is turned on initiating flooding phase which lasts on average 30 seconds.

Step 2: Swelling

Figure 5:
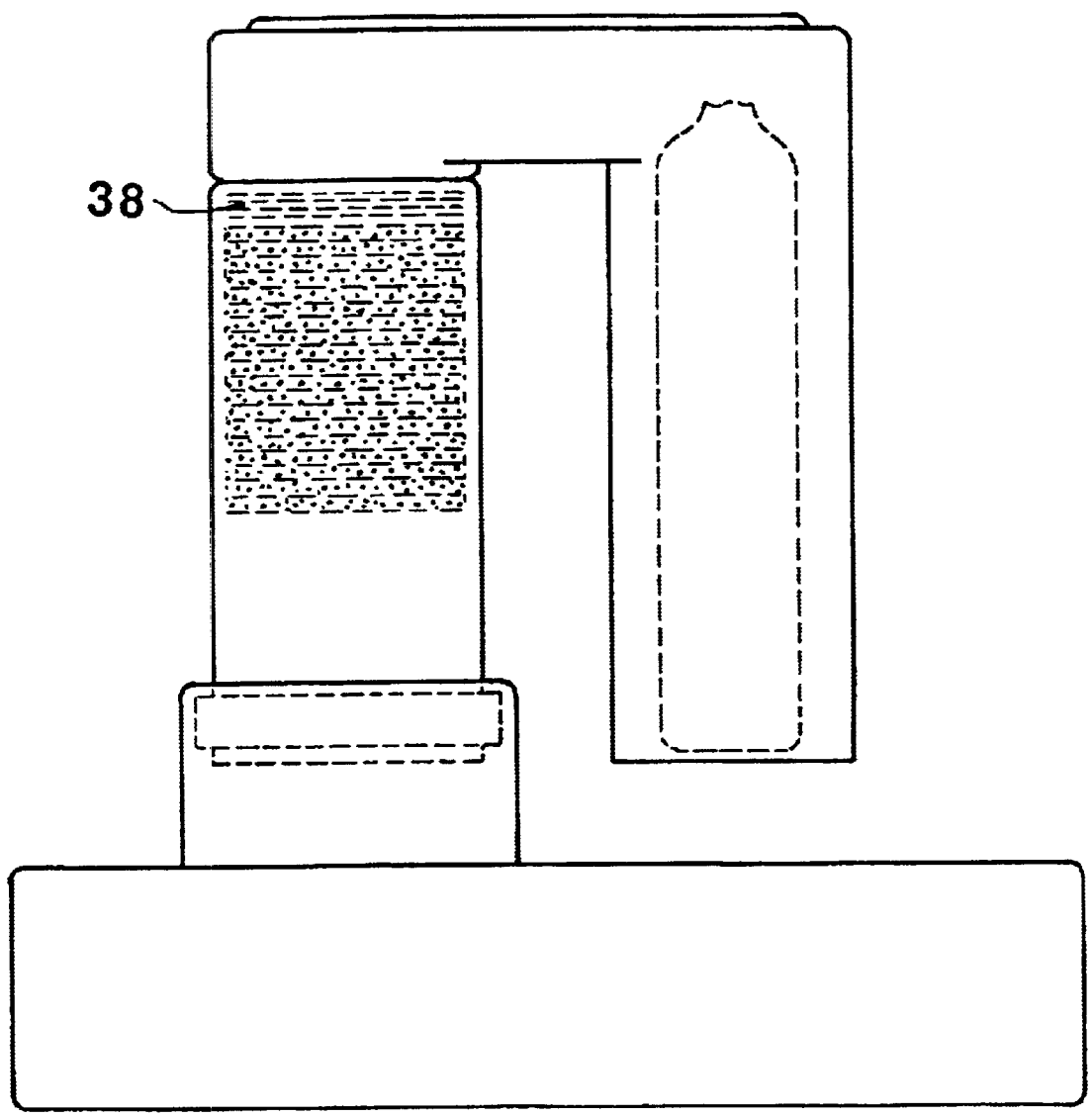
FIG. 5 is a schematic representation of the swelling phase of the bone cement.

Vacuum pump is turned off once the whole powder column has been flooded. Viscosity of the monomer reaching the outlet port 25 is increased and the flow of monomer through the gap between piston components 14 and 15 is very much slowed down. Thus the timing of the vacuum switch is not critical; some monomer is allowed to enter the labyrinth of the piston. Once the flooding is complete, the syringe is left in place for a pre-determined time (of 1,5 to 3,0 minutes, depending on the room temperature) of the waiting phase. During this time PMMA swells and dissolves in MMA. This releases benzoyl peroxide and initiates polymerization. Increased viscosity of the monomer due to dissolved polymer facilitates later extrusion of the cement mass; without this, rheological properties of the cement would resemble those of a wet sand. During swelling phase powder also settles down leaving an excess of monomer 38 at the top of the syringe as shown in FIG. 5.

Step 3: Draining

Figure 6:
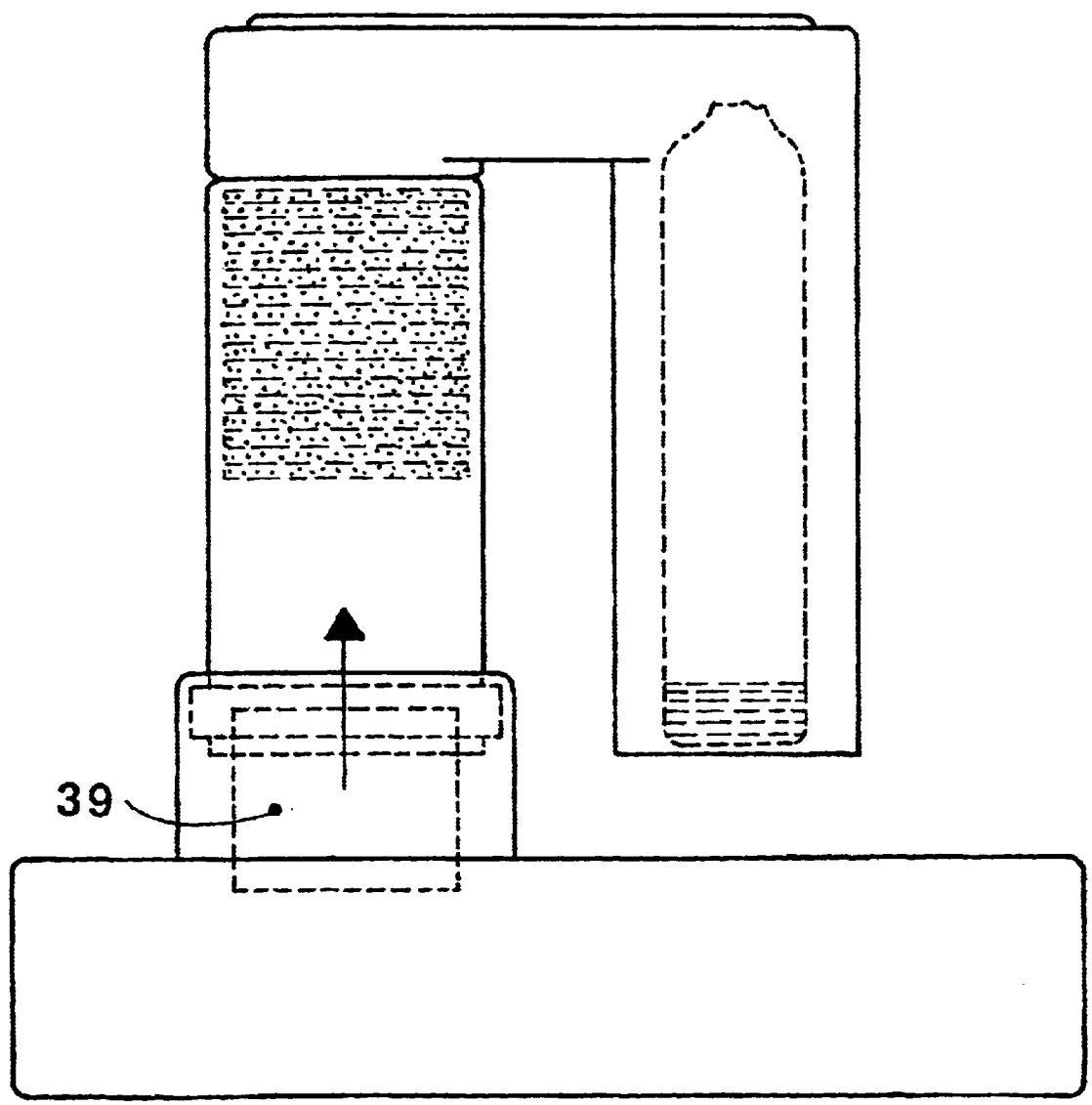
FIG. 6 is a schematic representation of the draining phase of the bone cement.

The excess monomer 38 collected at the top of the syringe, as well as minor air bubbles produced in the very early flooding, is returned through the mesh 19 back into the ampoule 21 by the action of a piston 39 in the pump 37, FIG. 6. Since neither the mesh 19 nor the piston gaps 25 allow escape of the powder particles, only the monomer is squeezed out from the cement mass as the piston 14/15 is advanced into the syringe 13. This phase, of about 15 to 30 seconds, is defined as draining. Note the principal difference to pressurizing as proposed by Draenart; in pressurizing no fluid is allowed to leave the cement mass.

Step 4: Extrusion

Figure 7:
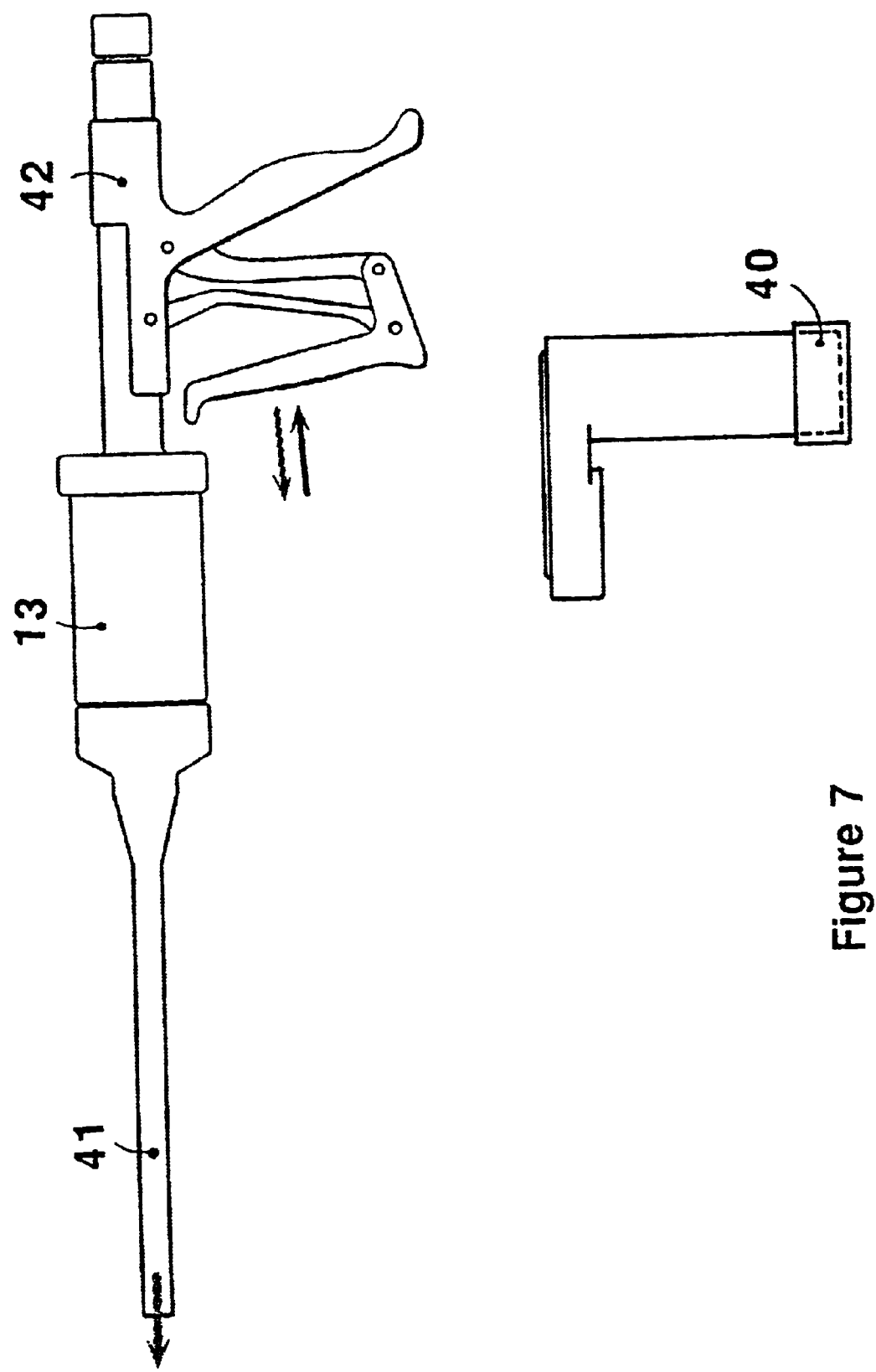
FIG. 7 is a schematic representation of showing the bone cement extrusion.

Once the excess monomer has been returned to the ampoule, adapter is removed from the syringe and disposed (covering the bottom with a disposal cap 40), a nozzle 41 is placed onto syringe 13, and the cement is extruded using a caulking gun 42 as shown in FIG. 7.

Figure 8:
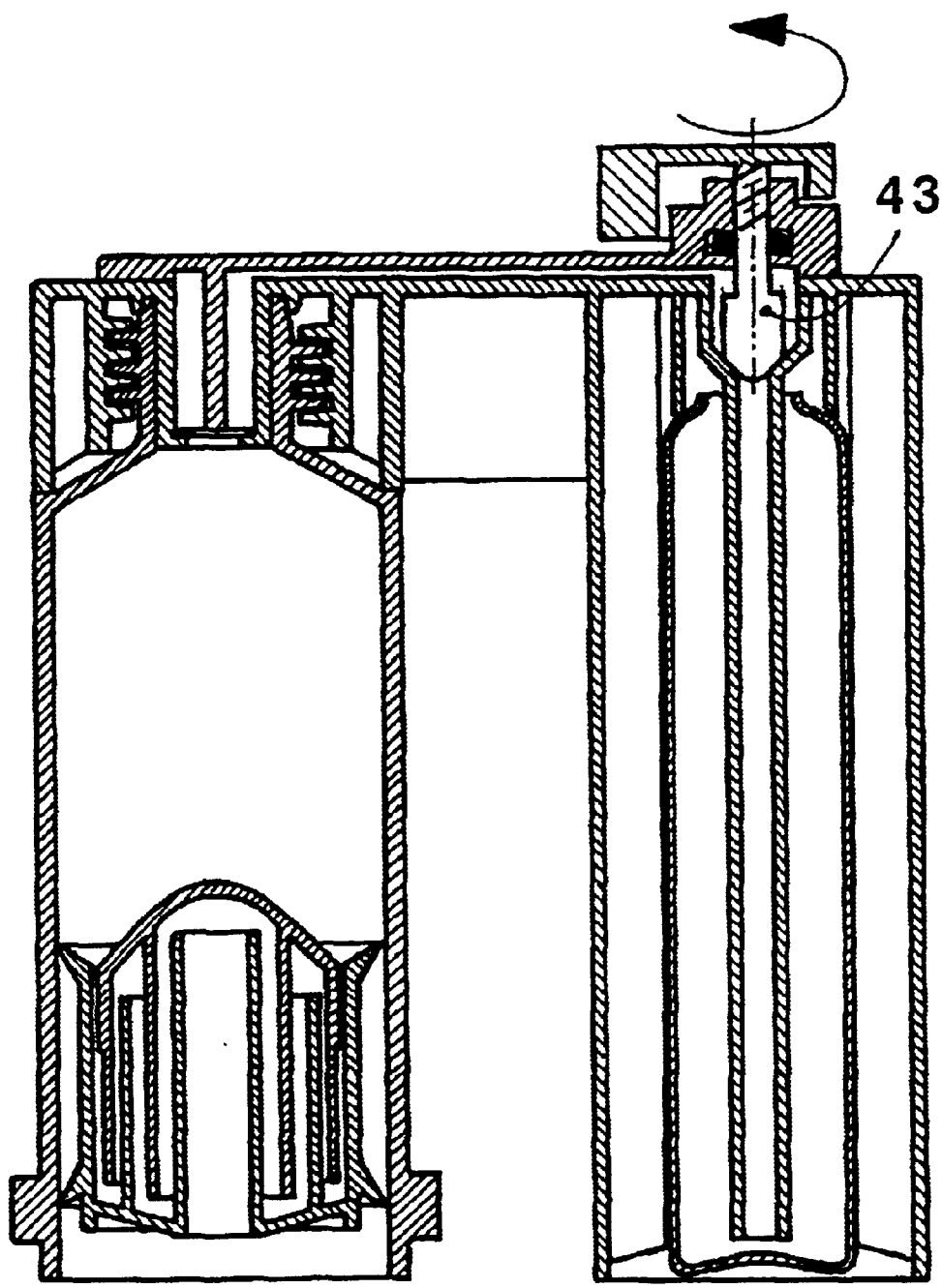
FIG. 8 is a section of the powder container with a valve of the apparatus according to the invention.

If the flooding is allowed to start with the first drop in pressure between the inlet port and the ampoule, some air will be trapped in the initial seconds of flooding. Most of it is expelled during draining. This initial entrapment of air can be reduced by a valve 43 inserted in the path of monomer, FIG. 8.

If this valve is opened with a delay of say 15 to 30 seconds after the vacuum is applied to the bottom of the syringe, monomer will start flooding of the powder column containing less residual air. A technically attractive placement of the valve is in the suction tube 17. The valve could also be made to open, mechanically or by rupture, by the pressure difference between the powder compartment and the ampoule.

Figure 9:
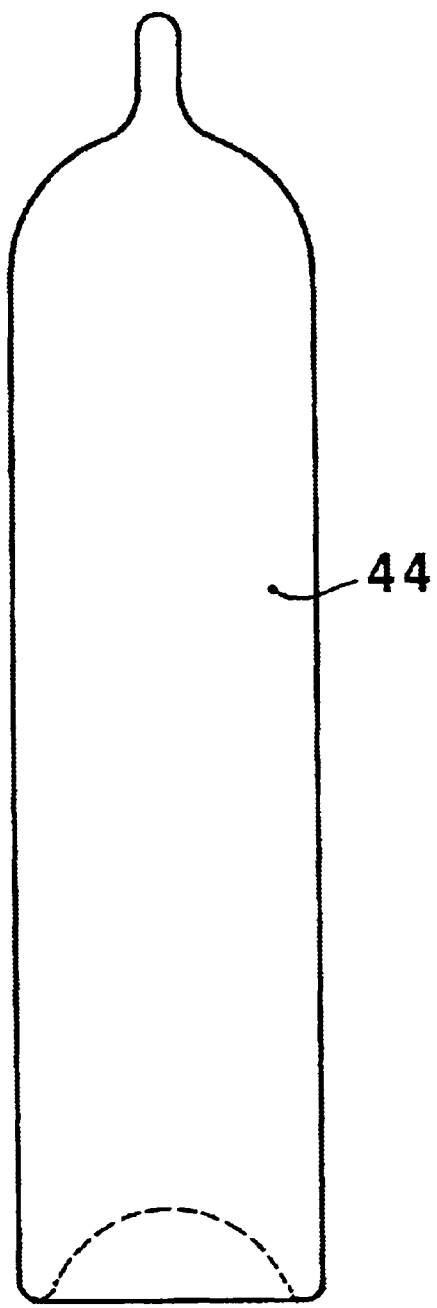
FIG. 9 is a schematic representation of an evacuated can as the source of vacuum for the method according to the invention.

An alternative to the vacuum pump is an evacuated can 44, FIG. 9. Evacuated to say below 1 mbar, the volume of such a can sufficient to drive the flooding is 0,3 to 0,5 liters. Such cans could be supplied sterile for single use, eliminating the need for cleaning and sterilization of (as well as the investment into) a vacuum pump. In this case draining operation could be performed by the caulking gun prior to extrusion.

Figure 10:
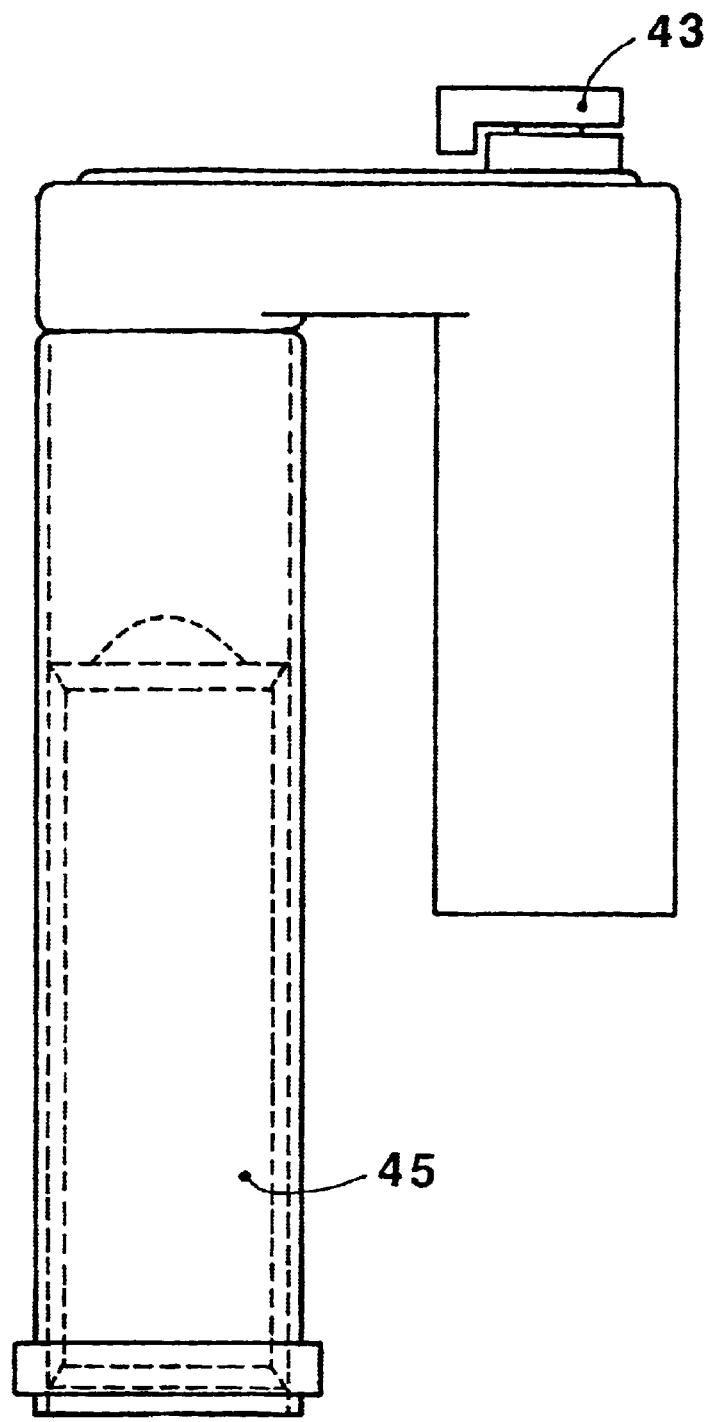
FIG. 10 is a schematic representation of a pre-evacuated package with a vacuum reservoir for use with the method according to the invention.

A method for preparing bone cement known from WO88/03811 TEPIC requires a high level of vacuum in the powder column in order to avoid incomplete flooding. Provision of two ports (8 and 9, FIG. 2) on the powder container, as in the current invention, and change in the basic concept of filling empty space by monomer to that of replacing residual air by monomer, allows for an integral source of vacuum—an enlarged piston 45, FIG. 10. Evacuation of the system could be effected through the inlet port which should then be sealed off, e.g. by a valve 43.

Advantages of the current invention have been demonstrated by extensive testing of mechanical and chemical properties of the bone cement prepared according to the invention. For comparison, most of the commercially available brands have been tested, as well as some preparations of bone cements based on the same formulation, but prepared by conventional means (hand mixing and partial vacuum mixing).

Release of the monomer into the operating room compared with the open, spatula-and-bowl mixing procedure, followed by kneading, is 60 times lower. Compared to a conventional partial vacuum mixing system, the release is 4 times lower. As commented earlier, the peak temperature is reduced by about 8 degrees C; shrinkage by about 1% absolute, i.e. by about 20% relative; residual monomer by about 20%.

Figure 11:
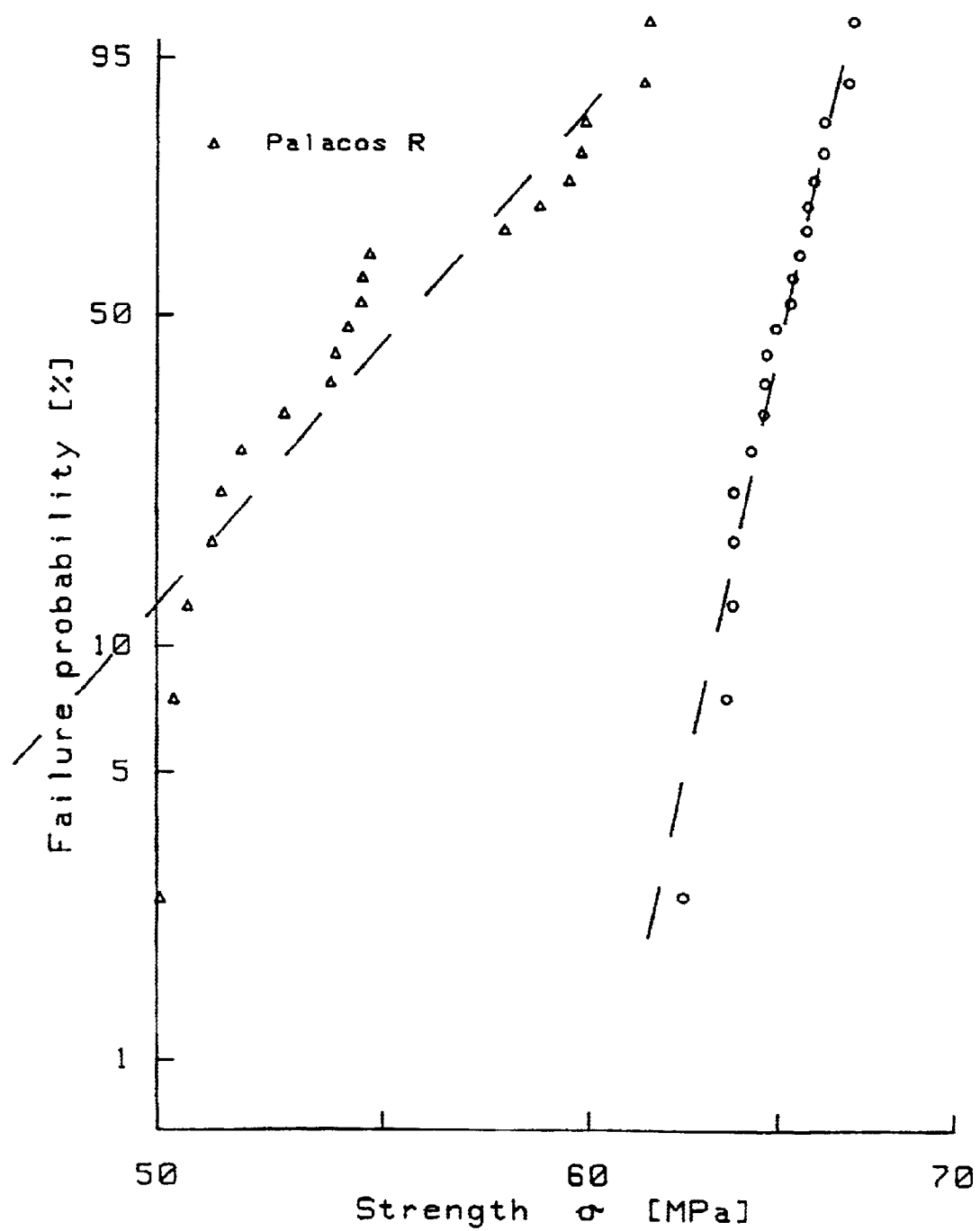
FIG. 11 shows a Weibull plot for the tensile strength of the bone cement obtained by the method according to invention vs. PALACOS R.

Tensile strength was measured to be 65 MPa compared with 40 to 55 MPa for all commercially available bone cements, hand mixed, or partial vacuum mixed. This is 20 to 60% higher and approaching the ultimate tensile strength of pure, block polymerized, PMMA (70 to 75 MPa). An important difference is also the greatly reduced variability as illustrated by Weibull plots of static tensile tests (bone cement according to current invention vs. PALACOS R) as shown in FIG. 11.

Intrinsic (without pores) fatigue strength (in bending) matches the best commercial bone cement (PALACOS R).

I claim:

1. A method of bone cement preparation from a polymeric powder and a liquid component, comprising a polymerisable monomer or comonomer, by action of a catalytic system, whereby particles of said powder component are packed in a powder container (7;35) with an inlet port (8) and an outlet port (9) and the liquid component is held in a liquid container (11), comprising the steps of:
   A) completely filling said powder container (7;35) with said polymeric powder;
   B) connecting said liquid container (11) to said inlet port (8);
   C) connecting a vacuum source (10) to said outlet port (9); and,
   D) completely flooding a void space between said particles of said powder component with said liquid component, said liquid component flowing from said inlet port (8) toward said outlet port (9) by the action of the vacuum source (10).

2. The method according to claim 1, wherein the catalytic system comprises benzoyl peroxide.

3. The method according to claim 1, wherein said upstream inlet port (8) and said downstream outlet port (9) of said container (7) allow air and liquid to pass therethrough, but not powder.

4. The method according to claim 1, wherein said powder container (7;35) is inflexible and in the form of a syringe (13).

5. The method according to claim 1, wherein said powder in said powder containing compartment (35) is packed to a fractional porosity of 0.34 to 0.38.

6. The method according to claim 5, wherein said powder in said powder containing compartment (35) is packed to a fractional porosity of 0.35 to 0.37.

7. The method according to claim 1, wherein said powder component is flooded by said liquid component in 15 to 60 seconds.

8. The method according to claim 7, wherein said powder component is flooded by said liquid component in 25 to 35 seconds.

9. The method according to claim 1, wherein the flow of said liquid component is controlled by a valve (12) interposed between said liquid container (11) and said inlet port (8).

10. The method according to claim 1, wherein flooding of said powder component by said liquid component is followed by swelling, draining of excess liquid component and extrusion of the mixed components.

11. The method according to claim 10, wherein said draining of excess liquid is effected by a piston (39) contained in a vacuum pump (37).

12. The method according to claim 1, wherein said inlet port (8) comprises a mesh (19) which prevents passage of said powder particles, but allows passage of said liquid.

13. The method according to claim 1, wherein said outlet port (9) comprises a narrow gap (25) that subsequently blocks passage of said powder particles, but allows for passage of air and said liquid.

14. The method according to claim 13, wherein the narrow gap (25) is smaller than 50 $\mu$.

15. The method according to claim 13, wherein the narrow gap (25) is smaller than 3 times an average diameter of said particles of said powder component.

16. The method according to claim 1, wherein said polymerisable monomer or comonomer comprises methyl-methacrylate, ethyl-methacrylate or butyl-methacrylate or mixtures thereof.

17. The method according to claim 1, wherein said vacuum source (10) generates a vacuum in the range of 10 to 200 mbar.

18. The method according to claim 17, wherein the vacuum source (10) generates a vacuum in the range of 50 to 100 mbar.

19. A method of bone cement preparation from a polymeric powder and a liquid component, comprising a polymerisable monomer or comonomer, by action of a catalytic system, whereby particles of said powder component are packed in a powder container (7;35) with an inlet port (8) and an outlet port (9) and the liquid component is held in a liquid container (11), comprising the steps of:

A) packing said powder in said powder container (7;35) to a fractional porosity of 0.30 to 0.43;

B) connecting the liquid container (11) to said inlet port (8);

C) connecting a vacuum source (10) to said outlet port (9); and,

D) flooding the void space between said particles of said powder component by said liquid component, said liquid component flowing from said inlet port (8) toward said outlet port (9) by the action of the vacuum source (10).

* * * * *